United States Patent [19]
Schulz et al.

[11] Patent Number: 6,008,422
[45] Date of Patent: Dec. 28, 1999

[54] ALKYLATION PROCESS USING INTERBED RECYCLING OF COOLED REACTOR EFFLUENT

[75] Inventors: Russell C. Schulz, Glen Ellyn; Perry K. Ho, Wheeling, both of Ill.

[73] Assignee: UOP LLC, Des Plaines, Ill.

[21] Appl. No.: 09/111,230

[22] Filed: Jul. 7, 1998

Related U.S. Application Data

[60] Provisional application No. 60/052,481, Jul. 14, 1997.
[51] Int. Cl.[6] .................................. C07C 2/64; C07C 2/68
[52] U.S. Cl. .......................... 585/449; 585/450; 585/453; 585/467
[58] Field of Search .................................. 585/449, 450, 585/453, 467

*Primary Examiner*—Walter D. Griffin
*Assistant Examiner*—In Suk Bullock
*Attorney, Agent, or Firm*—Thomas K. McBride; John G. Tolomei; Michael A. Moore

[57] ABSTRACT

A process for producing alkylaromatics using a multibed alkylation reaction zone is disclosed. The alkylation reaction zone effluent is divided into three portions, the first being recirculated to the inlet of the reaction zone, the second being cooled and recirculated to one or more other beds in the reaction zone, and the third being passed to a product recovery zone where the alkylaromatic is recovered. This process insures that all of the catalyst beds operate in an optimum temperature range. This in turn insures that byproduct formation is minimized and catalyst life is maximized. Ethylbenzene and cumene may be produced by this process.

15 Claims, 1 Drawing Sheet

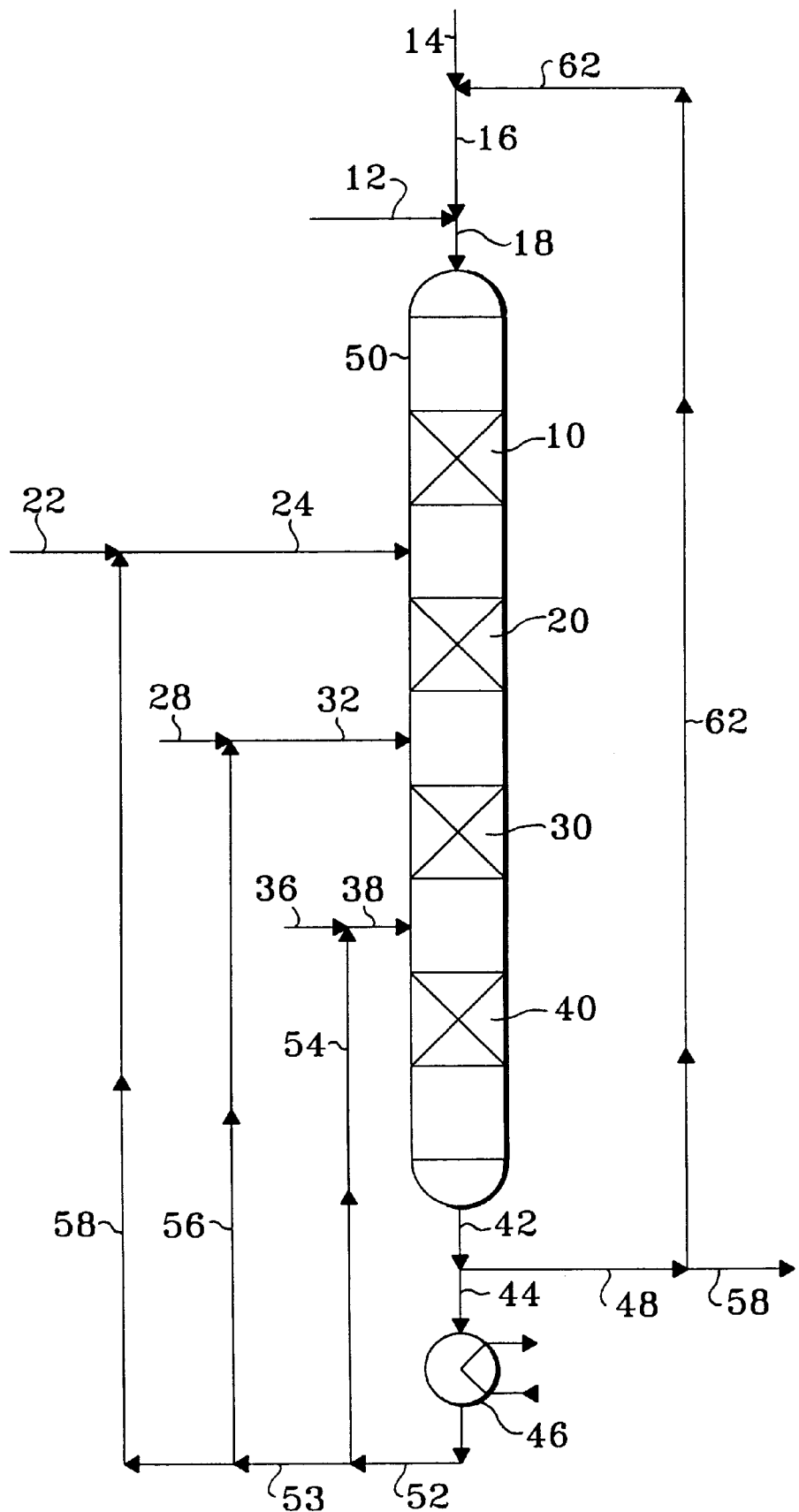

ALKYLATION PROCESS USING INTERBED RECYCLING OF COOLED REACTOR EFFLUENT

CROSS-REFERENCE TO RELATED APPLICATION

This application claims the benefit of U.S. Provisional Application No. 60/052,481, filed on Jul. 14, 1997.

FIELD OF THE INVENTION

This invention relates to a hydrocarbon conversion process. The invention more specifically relates to the production of alkylaromatic hydrocarbons by the reaction of an acyclic olefinic hydrocarbon with an aromatic feed hydrocarbon.

BACKGROUND OF THE INVENTION

The alkylation of aromatics with olefins to produce monoalkyl aromatics is a well developed art which is practiced commercially in large industrial units. One commercial application of this process is the alkylation of benzene with ethylene to produce ethylbenzene which is subsequently used to produce styrene. Another application is the alkylation of benzene with propylene to form cumene (isopropylbenzene) which is subsequently used in the production of phenol and acetone. Those skilled in the art are therefore familiar with the general design and operation of such alkylation processes.

Commercial cumene processes usually run with a molar ratio of phenyl groups per propyl group in the alkylation reactor that is greater than the stoichiometric ratio of 1:1 in order to avoid forming by-products. A high molar ratio primarily acts as a heat sink and controls the exothermic temperature rise in the reactor, thus reducing n-propylbenzene formation which is promoted at high temperature. Current specifications for n-propylbenzene in cumene product streams are in the range of 250 to 300 wppm, where wppm refers to parts of n-propylbenzene by weight per million parts of cumene by weight. A high molar ratio also reduces formation of diisopropylbenzene (DIPB) and triisopropylbenzene (TIPB) by polyalkylation and of propylene dimer and propylene trimer by oligomerization.

Prior art methods are known for controlling the temperature rise by using the excess benzene in the alkylation reactor effluent. The alkylation reactor effluent contains excess or unreacted benzene, of course, primarily because the molar ratio in the alkylation reactor is greater than stoichiometric. One prior art method distills this excess benzene from the reactor effluent and recycles a benzene stream to the inlet of the alkylation reactor, or to one or more of the reactor beds in the case of a multibed reactor. Another prior art method recycles some of the reactor effluent without separation to the inlet of the alkylation reactor. Both prior art methods leave room for improvement. In the former method, distilling benzene from the reactor effluent wastefully consumes utilities used in vaporizing and condensing benzene. In the latter method, recycling reactor effluent to the alkylation reactor inlet requires a large quantity of reactor effluent recycle to all of the reactor beds.

Not only must excessively high temperatures in the alkylation reactor be prevented, but excessively low temperatures must be avoided as well. For solid cumene alkylation catalysts, low temperatures accelerate catalyst deactivation by allowing heavy polyalkyl aromatics to deposit in the catalyst pores. Rapid deactivation shortens the catalyst life and necessitates more frequent shutdowns for the catalyst to be regenerated or replaced, thereby hurting the profitability of the cumene process.

Thus, a method is sought for preventing excessive temperatures, both high and low, in a multibed cumene alkylation reactor while efficiently using the excess benzene in the alkylation reactor effluent.

SUMMARY OF THE INVENTION

This invention recycles the effluent of a multibed alkylation reactor not only to the first bed, that is the reactor inlet, but also to one or more other beds. This invention uses a staged recycle arrangement, with different aliquot portions of the reactor effluent recycling to different beds in a series of beds. This invention keeps the temperature of each bed within an optimum operating range that minimizes n-propylbenzene formation and maximizes catalyst life. In addition, this invention permits the reactor effluent that is recycled to each bed to be cooled to much lower temperatures than are possible in processes where the reactor effluent is recycled only to the first bed. Thus, this invention significantly decreases the quantity of recycled effluent that is needed to control the temperature rise in the reactor beds.

Another advantage of this invention is a reduction in the capital expense, and possibly the mechanical complexity as well, of multibed alkylation reactors. Because this invention controls bed temperatures without indirect heat exchange of the effluent of any bed except the last bed, all of the alkylation catalyst beds may be in the same alkylation reaction vessel. In prior art processes more than one reaction vessel was needed, because the effluent stream of beds other than that of the last bed had to be cooled indirectly, and because it is usually simpler and less expensive to cool a stream using an indirect heat exchanger that is external rather than internal to a reaction vessel. It is believed that a process that uses multiple reaction beds will require less capital expense and be less mechanically complex when all of the reaction beds are in a single, common reaction vessel.

Accordingly, in one embodiment, this invention is a process for producing an alkyl aromatic. An aromatic substrate and an alkylating agent are contacted under alkylation conditions over a solid alkylation catalyst in a multibed reactor. An alkylation effluent comprising an alkyl aromatic is formed. A first aliquot portion of the alkylation effluent is recycled to a first bed of the reactor. A second aliquot portion of the alkylation effluent is cooled, and the cooled second aliquot portion is recycled to a second bed of the reactor. The second bed of the reactor is downstream relative to the first bed of the reactor. The alkyl aromatic is recovered from a third aliquot portion of the effluent stream.

In a more specific embodiment, this invention is a process for producing cumene. Propylene, benzene, and a hot recycle stream are passed to a first bed of a reaction zone. In the first bed, benzene is alkylated with propylene in the presence of zeolite beta catalyst to produce cumene. A first bed outlet stream comprising benzene and cumene is withdrawn from the first bed. At least a portion of the first bed outlet stream, a first portion of a cool recycle stream, and propylene are passed to a second bed of the reaction zone. In the second bed, benzene is alkylated with propylene in the presence of zeolite beta catalyst to produce cumene. A second bed outlet stream comprising benzene and cumene is withdrawn from the second bed. At least a portion of the second bed outlet stream, a second portion of the cool recycle stream, and propylene are passed to a third bed of the reaction zone. In the third bed, benzene is alkylated with propylene in the presence of zeolite beta catalyst to produce cumene. A third bed outlet stream comprising benzene and cumene is withdrawn from the third bed. At least a portion of the third bed outlet stream, a third portion of the cool recycle stream, and propylene are passed to a fourth bed of the reaction zone. In the fourth bed, benzene is alkylated with propylene in the presence of zeolite beta catalyst to produce cumene. An effluent stream comprising cumene is collected from the fourth bed. The hot recycle stream is formed from a first aliquot portion of the effluent stream. A second aliquot portion of the effluent stream is cooled to produce the cool recycle stream. Cumene is recovered from a third aliquot portion of the effluent stream.

INFORMATION DISCLOSURE

U.S. Pat. No. 4,051,191 describes catalysts, reaction conditions, and a separation method for the recovery of cumene that uses a rectification zone and a two-column fractionation train.

U.S. Pat. Nos. 4,695,665 and 4,587,370 are particularly directed to the separation of products and the recovery of recycle streams from processes for the alkylation of aromatic hydrocarbons, and U.S. Pat. No. 4,695,665 discloses the use of a flash drum in combination with an effluent rectifier to recover unreacted feed components.

U.S. Pat. No. 4,891,458 describes the use of beta zeolite for the alkylation of aromatic hydrocarbons with alkenes to produce alkyl aromatics. U.S. Pat. No. 4,891,458 also discloses that transalkylation can occur in an alkylation reactor, and that additional monoalkyl aromatic hydrocarbons can be produced in an alkylation reactor by recycling polyalkyl aromatic hydrocarbons to the alkylation reactor to undergo transalkylation.

U.S. Pat. No. 4,922,053 describes a process for alkylating benzene with ethylene in a multibed reactor wherein polyethylbenzenes are recycled to the first alkylation bed and also to one or more of the other alkylation beds in order to increase ethylbenzene yield.

U.S. Pat. No. 5,030,786 discloses an alkylation process wherein the feed stream is dehydrated to enhance the performance of beta or Y zeolites in the alkylation process.

U.S. Pat. No. 5,336,821 describes the use of beta zeolite for the alkylation of aromatic hydrocarbons in a process that is improved by an indirect heat exchanger to recover the heat of reaction. In one embodiment, the alkylation reactor effluent passes through the heat exchanger and is recycled to the alkylation reactor.

U.S. Pat. No. 4,008,290 describes a combination process that produces alkyl aromatic products by using an alkylation reaction zone and a transalkylation reaction zone. The alkylation effluent and the transalkylation effluent are passed to a common separation zone, which produces a recycle benzene stream. A portion of the alkylation effluent is recycled to the alkylation reaction zone in order to decrease the portion of the recycle benzene stream that is recycled to the alkylation reaction zone. The teachings of U.S. Pat. No. 4,008,290 are incorporated herein by reference.

U.S. Pat. No. 5,003,119 discloses a combination process for producing monoalkyl aromatics and describes passing dialkyl aromatics to the alkylation reaction zone.

BRIEF DESCRIPTION OF THE DRAWING

The FIGURE is a process flow diagram of one embodiment of the invention.

DETAILED DESCRIPTION OF THE INVENTION

This invention is suitable generally for alkylation substrate feeds and alkylation agent feeds, and more specifically to aromatic alkylation substrates and olefinic alkylating agents. Benzene is the aromatic alkylation substrate of principal interest, but alkyl-substituted benzenes may be used. More than one aromatic feed may be used. Monoolefins are the principal olefinic alkylating agent, but other diolefins, polyolefins, acetylenic hydrocarbons, and substituted hydrocarbons can be used. The olefinic alkylating agent preferably contains from 2 to 4 carbon atoms, but olefins having from 2 to 20 carbon atoms may be used. Ethylene and propylene are the preferred olefinic alkylating agents. More than one olefin may be used.

The most widely practiced hydrocarbon conversion process to which this invention is applicable is the production of cumene by alkylation of benzene with propylene. Therefore, the discussion herein of this invention refers mainly to cumene processes. It is not intended that this discussion limit the scope of this invention as set forth in the claims.

A catalyst promotes the initial alkylation in the alkylation reaction zone. A wide variety of catalysts can be used in the alkylation reaction zone. Suitable catalysts for use in the alkylation reaction zone comprise any catalyst that is not deactivated rapidly as a consequence of recycling reactor Effluent. In addition, the presence of cumene or other components of the reactor effluent should not have a deleterious effect on the approach to equilibrium cumene concentrations in the alkylation reaction zone.

The catalyst for the present invention may be one of a class of aluminosilicate molecular sieves known as zeolites. The zeolitic molecular sieves suitable for use in the present invention are crystalline aluminosilicates which in the calcined form may be represented by the general formula:

$$Me_{2/n}O:Al_2O_3:xSiO_2:yH_2O$$

where Me is a cation, n is the valence of the cation, x has a value of from about 5 to 100, and y has a value of from about 2 to 10.

Typical well known zeolites which may be used include zeolite X, zeolite Y, Linde Type L, medium pore ZSM-type zeolites such as ZSM-5, mordenite, omega, and beta. Detailed descriptions of zeolites may be found in D. W. Breck, *Zeolite Molecular Sieves,* John Wiley and Sons, New York 1974, and in other standard references. Preferred zeolites for use in the present invention are rare earth exchanged Y and steam stabilized Y zeolites as disclosed in U.S. Pat. No. 4,459,426 and zeolite beta as disclosed in U.S. Pat. Nos. 4,891,458 and 5,081,323, the teachings of which are incorporated herein by reference. It is believed that zeolite Y can also be a suitable zeolite for this invention.

The zeolite catalyst will usually be used in combination with a refractory inorganic oxide binder. The preferred inorganic oxide is alumina, with gamma-alumina, eta-alumina, and mixtures thereof being particularly preferred. Preferred binders are alumina and silica. The zeolite will usually be present in an amount of at least 50 wt-% of the catalyst, and preferably in an amount of at least 70 wt-% of the catalyst.

The alkylation reaction zone can operate over a broad range of operating conditions. In cumene processes the operating conditions preferably result in nearly equilibrium concentrations of cumene being produced in the alkylation reaction zone. The concentration of cumene is generally greater than 80% of the equilibrium concentration, and preferably greater than 95%. The alkylation reaction zone is ordinarily operated to obtain an essentially complete conversion of the alkylating agent (propylene) to cumene, diisopropylbenzene, or heavier polyisopropylbenzenes. Propylene conversion is generally more than 99.5% and preferably more than 99.9%. To help attain such high propylene conversion, a stoichiometric excess of benzene over propylene is generally present in alkylation reaction zone feed. The molar ratio of benzene per propylene is generally from 20:1 to 1:1, and preferably from 5:1 to 1:1. The molar ratio of phenyl groups per propyl group in the alkylation reaction zone is generally from 20:1 to 1:1, and preferably from 5:1 to 1:1. Temperatures usually range from 210 to 620° F. (99 to 327° C.) with the range of about 280 to 400° F. (138 to 204° C.) being preferred. The temperature rise in each bed of the alkylation reaction zone is preferably not more than 22° F. (12° C.). Pressures can also vary within a wide range of about 1 atmosphere to about 130 atmospheres. Because liquid phase conditions are generally preferred within the alkylation reaction zone, the pressure should be sufficient to maintain the benzene at least partially in a liquid phase and will typically fall in a range of from 10 to 50 atmospheres. The benzene liquid hourly space velocity (LHSV) is generally from about 0.5 to 50 $hr^{-1}$, and preferably from about 1 to 10 $hr^{-1}$. The water concentration in the alkylation reaction zone is generally greater than 50 wppm, but may be over 500 wppm, depending on the particular catalyst. The propylene concentration in the alkylation reaction zone is generally less than 10 mol-% and preferably less than 3 mol-%.

This invention is usually suitable to the case where the alkylating agent contains non-alkylating materials and preferably in low concentrations. For example, in a cumene process the propylene-containing stream commonly contains some propane. This invention is applicable where the propylene stream contains from 0 to about 90 wt-% propane, and preferably from 0 to about 40 wt-% propane.

As mentioned previously, an essential element of this invention is recycling a cooled aliquot portion of the reactor effluent to one or more of the alkylation catalyst beds downstream of the first catalyst bed. For a given quantity of catalyst in an alkylation reactor, the rate of effluent recycle is a function of the number of catalyst beds, the temperature of the effluent recycle, the desired inlet temperature of each bed, the percentage of the total amount of catalyst in each bed, and the percentage of the total amount of alkylating agent (e.g., propylene) to each bed. As the number of beds increases, the required recycle rate usually decreases. This is because a large number of catalyst beds results in a relatively small amount of catalyst in each bed, and hence a small amount of alkylating agent (e.g., propylene) to each bed. This in turn results in a relatively small temperature rise because less exothermic heat of reaction is generated. Consequently, less effluent recycle is necessary to control the relatively small temperature rise that occurs in each of the small beds. This invention is suitable for alkylation reaction zones having at least two catalyst beds in series, and it is believed that a benefit in accord with this invention can be obtained in alkylation reaction zones having up to 18 catalyst beds in series. The optimum number of catalyst beds in series is believed to be between 4 and 8 catalyst beds, and preferably 6 catalyst beds. As the temperature of the effluent recycle decreases, the required recycle rate usually decreases. The recycled effluent is cooled to a temperature of generally from 35° F. to 300° F., and usually from 100° F. to 150° F. Regarding the desired inlet temperature of each catalyst bed, the lower the desired temperature the greater is the required amount of cooled recycled reactor effluent. Finally, with respect to the percentage of total catalyst in each bed, as the percentage in a bed decreases the amount of effluent recycle for maintaining optimum bed temperatures in that bed decreases.

Generally, the ratio of the amount of total recycled reactor effluent to the net (that is, non-recycled) amount of reactor effluent is generally less than 5:1 and preferably less than 3:1, and more preferably less than 3:1 and greater than 1:1. Of the total recycled amount of effluent, an aliquot portion is passed without cooling to the inlet of the alkylation reactor, that is to the first bed. One or more other aliquot portions of the reactor effluent are cooled and then recycled to one or more other catalyst beds. Where more than one aliquot portion of the reactor effluent is cooled and recycled, the reactor effluent may be cooled before being divided into aliquot portions, or the reactor effluent may be divided into aliquot portions before being cooled individually, or a combination of both. Generally, between 5 and 75% of the total recycled reactor effluent passes to the first bed, and the remaining 95% to 25% passes after cooling to the other catalyst beds. The proportion of the total recycled amount of reactor effluent that flows to any particular catalyst bed is from 5% to 75% of the total recycled reactor effluent.

The alkylation reaction zone may be operated and arranged in any manner that provides the desired operating temperatures and number of contacting stages. Multiple contacting stages in the alkylation reaction zone are routinely used to provide cooling by staged addition of reactants to multiple beds of alkylation catalyst. The multiple injection of the reactants serves to cool the stages between alkylation catalyst beds, to reduce the propylene concentration, and to provide temperature control. The alkylation catalyst is ordinarily arranged in multiple beds to permit interbed injection of propylene. The separate alkylation catalyst beds may be arranged in a single vessel or in multiple vessels. There is no requirement that the alkylation catalyst beds be in separate alkylation reactor vessels.

The alkylation effluent generally is a mixture of cumene, benzene which is ordinarily present in a stoichiometric excess, and a wide variety of undesired by-products, such as polyisopropylbenzenes, other heavy alkylated aromatics, and propylene condensation by-products. Therefore, a number of separation stages are needed to separate the desired alkyl aromatic product (cumene) from the by-products and excess aromatic substrate (benzene). The present invention may use any combination of columns and separators to recover the desired alkyl aromatic product and, if desired, to produce streams of aromatic substrate and polyalkyl aromatics.

This invention may use a transalkylation reaction zone. As stated, the alkylation reaction zone produces polyalkyl aromatics as well as the desired monoalkyl aromatic. Therefore, in some embodiments of this invention these polyalkyl aromatics can contact additional aromatic substrate in a transalkylation reactor to produce additional monoalkyl aromatic. Diisopropylbenzene and higher polyisopropylbenzenes transalkylate with benzene to produce cumene (isopropylbenzene) in the transalkylation reaction zone. Generally, a catalyst promotes the transalkylation in the transalkylation reaction zone. Suitable transalkylation processes, catalysts, operating conditions, and product recovery facilities are known to persons of ordinary skill in the art of hydrocarbon processing. Where a transalkylation zone is used, this invention is not limited to any particular transalkylation zone or transalkylation catalyst. The transalkylation reaction zone and the alkylation reaction zone may be in the same or separate vessels.

FIG. 1 illustrates an embodiment of the invention for the production of cumene. For clarity and simplicity, some items associated with the operation of the process have not been shown. These items include flow and pressure control valves, pumps, heat exchangers, temperature and pressure monitoring systems, reactor internals, etc., which may be of customary design. FIG. 1 is not intended to limit the scope of the present invention as set forth in the claims.

Referring now to FIG. 1, fresh or recycle benzene flows through a line 14 and mixes with a stream in a line 62 that contains a recycled portion of the reactor effluent from an alkylation reactor 50. The mixture flows through a line 16, receives propylene from a line 12, and enters the alkylation reactor 50 through a line 18. Alkylation reactor 50 houses four alkylation beds, 10, 20, 30, and 40, which are in series and which all contain zeolitic alkylation catalyst. The effluent from bed 10 continues to flow through reactor 50. Line 22 supplies propylene and line 58 supplies a cooled, recycled aliquot portion of the effluent of reactor 50 to a line 24. The line 24 passes the mixture of propylene and reactor effluent into reactor 50, where it combines with the effluent of bed 10 and contacts the catalyst in the bed 20.

Line 28 supplies propylene for the alkylation bed 30. The propylene for bed 30 flows through lines 28 and 32 and enters reactor 50 upstream of bed 30. Line 56 recycles cooled alkylation effluent from reactor 50 for the alkylation bed 30. Cooled alkylation effluent for bed 30 flows through lines 56 and 32 and enters reactor 50 upstream of bed 30. Thus, the line 32 passes a mixture of propylene and reactor effluent into reactor 50, where it combines with the effluent of bed 20 and contacts the catalyst in the bed 30.

Propylene for bed 40 flows through lines 36 and 38 and enters upstream of bed 40, and another aliquot portion of cooled alkylation Effluent flows through lines 54 and 38 and also enters upstream of bed 40. The effluent of bed 30 continues to flow through reactor 50, combines with the mixture that enters reactor 50 via the line 38, and contacts the catalyst in bed 40. Reaction zone effluent from alkylation bed 40 flows from reactor 50 via a line 42.

The line 42 from reactor 50 supplies alkylation zone effluent to the four alkylation catalyst beds 10, 20, 30, and 40, and also to a Fractionation section. The aliquot portion of the effluent for the fractionation section flows from the line 42 and through lines 48 and 58 to the fractionation section, which is not shown in the FIGURE. The aliquot portion of the effluent for bed 10 flows from line 42 and through lines 48 and 62, and then through lines 16 and 18 as described previously. Another aliquot portion of the effluent flows from line 42 and through line 44 and is cooled by indirect heat exchanger 46. Exchanger 46 removes some of the exothermic heat of the alkylation reaction. The cooling medium of heat exchanger 46 that receives heat from the effluent stream may be any suitable cool stream, such as cooling water, ambient air, or the fresh or recycle benzene that flows through the line 14. The cooled effluent flows from exchanger 46 via a line 52. Line 52 supplies aliquot portions of cooled effluent to bed 20 via lines 53, 58, and 24; to bed 30 via lines 53, 56 and 32; and to bed 40 via lines 54 and 38.

The beneficial operation of this invention will be further described in the context of two examples that exemplify a preferred embodiment, which is the alkylation of propylene with benzene to produce cumene. Both Examples I and II are based on engineering calculations and actual operating experience with similar processes. In describing these examples, valves, pumps, feeders, instruments, and heat exchangers other than those necessary for an understanding and appreciation of the invention have been omitted.

EXAMPLE I

The flow scheme for Example I is substantially that shown in the FIGURE. Example I shows the effect on the reactor bed temperatures of recycling an aliquot portion of reactor 60 effluent to bed 10 and aliquot portions of cooled reactor 60 effluent to beds 20, 30, and 40. Beds 10, 20, 30, and 40 each contain 25% of the total amount of catalyst in reactors 50 and 60. Table 1 shows that 48.9% of the reactor 60 effluent flows to bed 10, 14.7% to bed 20, 16.6% to bed 30, and the remaining 19.8% to bed 40. Table 1 shows that the temperature of the recycled effluent for bed 10 is 299° F. (148° C.), and that of the cooled recycled effluent for beds 20, 30, and 40 is 150° F. (66° C.).

Table 1 shows that for Example I the temperatures of all four beds remain within the optimum range of from 277 to 299° F. (136 to 148° C.). The exothermic temperature rise in each of reactors 10, 20, and 30 is compensated for by a corresponding drop in temperature as a result of introducing the cooled effluent upstream of reactors 20, 30, and 40, respectively. A cumene process operating as in Example I will form a relatively small amount of n-propylbenzene and will exhibit a relatively long catalyst life. The amount of n-propylbenzene produced divided by the amount of cumene produced, across the alkylation reactor 50 in Example I, is 0.000181. In addition, even though the benzene and propylene feed rates are the same in Examples I and II, Example I requires about 70% less recycled reactor 50 effluent than Example II.

EXAMPLE II

The flow scheme for Example II is the same as that shown in the FIGURE and described previously, except that the innovation of this invention is not employed. More specifically, the flow scheme for Example II is that shown in the FIGURE, except that line 44, exchanger 46, and lines 52, 53, 54, 56, and 58 are deleted. Accordingly, no cooled recycled effluent passes to beds 20, 30, and 40. In addition, instead of one reactor 50 containing all four alkylation beds 10, 20, 30, and 40, in Example II alkylation beds 10 and 20 are housed in a separate reactor from alkylation beds 30 and 40. The bed 20 effluent, which is the effluent of the first reactor, passes to an indirect heat exchanger to remove the exothermic heat of reaction by removing heat from the effluent of the first reactor. After having been cooled in the indirect heat exchanger, the cooled first reactor effluent passes to the second reactor and enters bed 30.

Example II shows the 70% higher reactor effluent recycle rate that results when there is no recycling of cooled reactor effluent to beds 20, 30, and 40, while maintaining the temperatures of all four beds within the optimum range of from 277 to 299° F. (136 to 148° C.). Beds 10, 20, 30, and 40 each contain 25% of the total amount of catalyst in the reactors. Table 1 shows that 100% of the reactor effluent flows to bed 10. Table 1 also shows that the temperature of the recycled effluent for bed 10 is 299° F., which is the same as in Example I. The release of exothermic heat in each bed causes a step-wise increase in bed temperature. Between beds 10 and 20 and between beds 30 and 40 there is no cooling by recycled reactor effluent, although a 2–3° F. temperature drop does occur because of the injection of propylene and because of heat losses. A cumene process operating as in Example II will form the same amount of n-propylbenzene and will exhibit the same catalyst life as in Example I, because the bed temperatures in Examples I and II are the same, but Example II requires 70% more reactor effluent recycle than Example I.

TABLE 1

Operating Conditions for Four Alkylation Beds for Examples I and II

|  | Example I | Example II |
|---|---|---|
| Minimum Number of Reactors | 1 | 2 |
| Benzene Feed Rate | Base | Base |
| Propylene Feed Rate | Base | Base |
| Reactor Effluent Recycle Rate | Base | 1.70 × Base |
| Temperature of Reactor Effluent Recycle to Beds 20, 30 and 40, °F. | 150 | NA |
| Staging of Reactor Effluent Recycle, as % of Reactor Effluent Recycle Rate: | | |
| To Bed 10 | 48.9 | 100 |
| To Bed 20 | 14.7 | 0 |
| To Bed 30 | 16.6 | 0 |
| To Bed 40 | 19.8 | 0 |
| Minimum Bed Temperature, °F. | 277 | 277 |
| Maximum Bed Temperature, °F. | 299 | 299 |
| (Δ n-propylbenzene/Δ cumene) Across Alkylation Reactor | 0.000181 | 0.000181 |

NA = Not Applicable

What is claimed is:

1. A process for producing an alkyl aromatic comprising the steps of:
   a) contacting an aromatic substrate and an alkylating agent under alkylation conditions over a solid alkylation catalyst in a multibed reactor to form an alkylation effluent comprising an alkyl aromatic;
   b) recycling a first aliquot portion of said alkylation effluent to a first bed of said reactor;
   c) cooling a second aliquot portion of said alkylation effluent to produce a cooled second aliquot portion, and recycling said cooled second aliquot portion to a second bed of said reactor that is downstream relative to said first bed of said reactor; and
   d) recovering said alkyl aromatic from a third aliquot portion of said effluent stream.

2. The process of claim 1 further characterized in that said process comprises the steps of:
   a) passing said aromatic substrate and said alkylating agent to said first bed, and withdrawing a first bed outlet stream comprising said alkyl aromatic from said first bed;
   b) passing at least a portion of said first bed outlet stream and said alkylating agent to said second bed, and withdrawing a second bed outlet stream comprising said alkyl aromatic from said second bed; and
   c) forming said alkylation effluent from at least a portion of said second bed outlet stream.

3. The process of claim 2 further characterized in said passing of said at least a portion of said first bed outlet stream to said second bed comprises the steps of:
   a) passing said at least a portion of said first bed outlet stream and said alkylating agent to a third bed, and withdrawing a third bed outlet stream comprising said alkyl aromatic from said third bed; and
   b) passing at least a portion of said third bed outlet stream to said second bed.

4. The process of claim 3 further characterized in that a fourth aliquot portion of said effluent stream is cooled to produce a cooled fourth aliquot portion, and said cooled fourth aliquot portion is recycled to said third bed.

5. The process of claim 1 wherein said aromatic substrate is benzene, said alkylating agent is ethylene, and said alkyl aromatic is ethylbenzene.

6. The process of claim 1 wherein said aromatic substrate is benzene, said alkylating agent is propylene, and said alkyl aromatic is cumene.

7. The process of claim 1 further characterized in that:
   a) said cooling of said second aliquot portion of said effluent stream comprises indirectly exchanging heat from said second aliquot portion to a feed stream comprising said aromatic substrate to produce a heated feed stream comprising said aromatic substrate; and
   b) providing at least a portion of the aromatic substrate in Step (a) of claim 1 from said heated feed stream.

8. The process of claim 1 further characterized in that said alkylating occurs under at least partial liquid phase conditions.

9. The process of claim 1 wherein said solid alkylation catalyst comprises zeolite beta.

10. The process of claim 1 further characterized in that said alkylation conditions comprise a temperature of from 210 to 620° F., and said cooled second aliquot portion of said effluent stream has a temperature of from 35 to 300° F.

11. The process of claim 1 further characterized in that said alkylation conditions comprise a temperature of from 277 to 299° F. and a temperature rise in said first or said second bed of not more than 22° F.

12. The process of claim 1 further characterized in that said cooled second aliquot portion has a temperature of from 100 to 150° F.

13. The process of claim 1 further characterized in that the ratio of the sum of said first aliquot portion and said second aliquot portion to said third aliquot portion is greater than 1:1.

14. A process for producing cumene, which comprises the steps of:
   a) passing propylene, benzene, and a hot recycle stream to a first bed of a reaction zone, alkylating benzene with propylene in the presence of zeolite beta catalyst in said first bed to produce cumene, and withdrawing a first bed outlet stream comprising benzene and cumene from said first bed;
   b) passing propylene, at least a portion of said first bed outlet stream, and a first portion of a cool recycle stream to a second bed of said reaction zone, alkylating benzene with propylene in the presence of zeolite beta catalyst in said second bed to produce cumene, and withdrawing a second bed outlet stream comprising benzene and cumene from said second bed;
   c) passing propylene, at least a portion of said second bed outlet stream, and a second portion of said cool recycle stream to a third bed of said reaction zone, alkylating benzene with propylene in the presence of zeolite beta catalyst in said third bed to produce cumene, and withdrawing a third bed outlet stream comprising benzene and cumene from said third bed;
   d) passing propylene, at least a portion of said third bed outlet stream, and a third portion of said cool recycle stream to a fourth bed of said reaction zone, alkylating benzene with propylene in the presence of zeolite beta catalyst in said fourth bed to produce cumene;
   e) collecting an effluent stream comprising cumene from said fourth bed;
   forming said hot recycle stream from a first aliquot portion of said effluent stream;
   g) cooling a second aliquot portion of said effluent stream to produce said cool recycle stream; and
   h) recovering cumene from a third aliquot portion of said effluent stream.

15. The process of claim 1 further characterized in that the first aliquot portion is recycled without cooling to said first bed of said reactor.

* * * * *